United States Patent
Schuelke et al.

(10) Patent No.: US 12,150,647 B2
(45) Date of Patent: Nov. 26, 2024

(54) METHOD FOR PUNCHING A LUMEN AND IMPLANTING AN IMPLANT DEVICE

(71) Applicant: Kardion GmbH, Stuttgart (DE)

(72) Inventors: Armin Schuelke, Aidlingen (DE); Hardy Baumbach, Stuttgart (DE); Inga Schellenberg, Stuttgart (DE); Tobias Bergem, Karlsruhe (DE)

(73) Assignee: Kardion GmbH, Stuttgart (DE)

( * ) Notice: Subject to any disclaimer, the term of this patent is extended or adjusted under 35 U.S.C. 154(b) by 873 days.

(21) Appl. No.: 17/222,842

(22) Filed: Apr. 5, 2021

(65) Prior Publication Data
US 2021/0322011 A1  Oct. 21, 2021

Related U.S. Application Data

(62) Division of application No. 15/613,409, filed on Jun. 5, 2017, now Pat. No. 11,000,282.

(30) Foreign Application Priority Data

Jun. 6, 2016  (DE) .......................... 102016209871.3

(51) Int. Cl.
*A61B 17/11* (2006.01)
*A61B 17/12* (2006.01)
(Continued)

(52) U.S. Cl.
CPC ........ *A61B 17/11* (2013.01); *A61B 17/12045* (2013.01); *A61B 17/32002* (2013.01);
(Continued)

(58) Field of Classification Search
CPC .............. A61B 17/11; A61B 17/32053; A61B 17/3209; A61B 17/32096; A61B 17/3423;
(Continued)

(56) References Cited

U.S. PATENT DOCUMENTS

| 2,254,698 A | 9/1941 | Hansen, Jr. |
| 3,085,407 A | 4/1963 | Tomlinson |

(Continued)

FOREIGN PATENT DOCUMENTS

| CA | 3 000 581 | 4/2017 |
| CN | 103143072 | 6/2013 |

(Continued)

OTHER PUBLICATIONS

Atkinson et al., "Pulse-Doppler Ultrasound and Its Clinical Application", The Yale Journal of Biology and Medicine, 1977, vol. 50, pp. 367-373.

(Continued)

*Primary Examiner* — Diane D Yabut
*Assistant Examiner* — Christian D Knauss
(74) *Attorney, Agent, or Firm* — Knobbe, Martens, Olson & Bear, LLP

(57) ABSTRACT

A punching device, for punching a lumen and implanting an implant device, includes at least the implant device for punching the lumen and for implantation into the lumen. In addition, the punching device includes an implantation device, a closure device, and an actuation device.

18 Claims, 5 Drawing Sheets

(51) Int. Cl.
*A61B 17/32* (2006.01)
*A61B 17/3205* (2006.01)
*A61M 39/00* (2006.01)
A61B 17/00 (2006.01)
A61B 17/34 (2006.01)

(52) U.S. Cl.
CPC ....... *A61B 17/32053* (2013.01); *A61M 39/00* (2013.01); *A61B 2017/00654* (2013.01); *A61B 2017/00659* (2013.01); *A61B 2017/1107* (2013.01); *A61B 2017/1135* (2013.01); *A61B 17/12036* (2013.01); *A61B 2017/320064* (2013.01); *A61B 2017/3454* (2013.01)

(58) Field of Classification Search
CPC ..... A61B 2017/1107; A61B 2017/1114; A61B 2017/1135; A61B 2017/9517; A61B 2017/3425; A61B 2017/3427; A61F 2/95; A61F 2/966; A61F 11/002; A61F 2/9517
See application file for complete search history.

(56) References Cited

U.S. PATENT DOCUMENTS

| | | |
|---|---|---|
| 3,614,181 A | 10/1971 | Meeks |
| 3,645,268 A * | 2/1972 | Capote ............ A61F 11/202 604/117 |
| 3,747,998 A | 7/1973 | Klein et al. |
| 3,790,878 A | 2/1974 | Brokaw |
| 3,807,813 A | 4/1974 | Milligan |
| 4,441,210 A | 4/1984 | Hochmair et al. |
| 4,888,009 A | 12/1989 | Lederman et al. |
| 4,888,011 A | 12/1989 | Kung et al. |
| 4,896,754 A | 1/1990 | Carlson et al. |
| 5,000,177 A | 3/1991 | Hoffmann et al. |
| 5,195,877 A | 3/1993 | Kletschka |
| 5,289,821 A | 3/1994 | Swartz |
| 5,443,503 A | 8/1995 | Yamane |
| 5,599,173 A | 2/1997 | Chen et al. |
| 5,613,935 A | 3/1997 | Jarvik |
| 5,629,661 A | 5/1997 | Ooi et al. |
| 5,690,674 A | 11/1997 | Diaz |
| 5,713,954 A | 2/1998 | Rosenberg et al. |
| 5,766,207 A | 6/1998 | Potter et al. |
| 5,814,900 A | 9/1998 | Esser |
| 5,843,141 A | 12/1998 | Bischoff et al. |
| 5,888,242 A | 3/1999 | Antaki et al. |
| 6,053,873 A | 4/2000 | Govari et al. |
| 6,058,958 A | 5/2000 | Benkowski et al. |
| 6,149,405 A | 11/2000 | Abe et al. |
| 6,212,430 B1 | 4/2001 | Kung et al. |
| 6,224,540 B1 | 5/2001 | Lederman et al. |
| 6,254,359 B1 | 7/2001 | Aber |
| 6,264,601 B1 | 7/2001 | Jassawalla et al. |
| 6,324,430 B1 | 11/2001 | Zarinetchi et al. |
| 6,324,431 B1 | 11/2001 | Zarinetchi et al. |
| 6,361,292 B1 | 3/2002 | Chang et al. |
| 6,366,817 B1 | 4/2002 | Kung |
| 6,389,318 B1 | 5/2002 | Zarinetchi et al. |
| 6,398,734 B1 | 6/2002 | Cimochowski et al. |
| 6,400,991 B1 | 6/2002 | Kung |
| 6,442,434 B1 | 8/2002 | Zarinetchi et al. |
| 6,445,956 B1 | 9/2002 | Laird et al. |
| 6,471,713 B1 * | 10/2002 | Vargas ............ A61B 17/11 606/153 |
| 6,496,733 B2 | 12/2002 | Zarinetchi et al. |
| 6,508,756 B1 | 1/2003 | Kung et al. |
| 6,516,227 B1 | 2/2003 | Meadows et al. |
| 6,527,698 B1 | 3/2003 | Kung et al. |
| 6,530,876 B1 | 3/2003 | Spence |
| 6,540,658 B1 | 4/2003 | Fasciano et al. |
| 6,553,263 B1 | 4/2003 | Meadows et al. |
| 6,561,975 B1 | 5/2003 | Pool et al. |
| 6,592,620 B1 | 7/2003 | Lancisi et al. |
| 6,979,338 B1 * | 12/2005 | Loshakove ............ A61B 17/11 606/153 |
| 7,062,331 B2 | 6/2006 | Zarinetchi et al. |
| 7,070,398 B2 | 7/2006 | Olsen et al. |
| 7,155,291 B2 | 12/2006 | Zarinetchi et al. |
| 7,160,243 B2 | 1/2007 | Medvedev |
| 7,338,521 B2 | 3/2008 | Antaki et al. |
| 7,513,864 B2 | 4/2009 | Kantrowitz et al. |
| 7,520,850 B2 | 4/2009 | Brockway |
| 7,762,941 B2 | 7/2010 | Jarvik |
| 7,794,384 B2 | 9/2010 | Sugiura et al. |
| 7,819,916 B2 | 10/2010 | Yaegashi |
| 7,942,805 B2 | 5/2011 | Shambaugh, Jr. |
| 7,959,551 B2 | 6/2011 | Jarvik |
| 8,012,079 B2 | 9/2011 | Delgado, III |
| 8,075,472 B2 | 12/2011 | Zilbershlag et al. |
| 8,088,059 B2 | 1/2012 | Jarvik |
| 8,231,519 B2 | 7/2012 | Reichenbach et al. |
| 8,489,200 B2 | 7/2013 | Zarinetchi et al. |
| 8,608,635 B2 | 12/2013 | Yomtov et al. |
| 8,612,002 B2 | 12/2013 | Faltys et al. |
| 8,620,447 B2 | 12/2013 | D'Ambrosio et al. |
| 8,766,788 B2 | 7/2014 | D'Ambrosio |
| 8,827,890 B2 | 9/2014 | Lee et al. |
| 8,862,232 B2 | 10/2014 | Zarinetchi et al. |
| 8,870,739 B2 | 10/2014 | LaRose et al. |
| 8,900,114 B2 | 12/2014 | Tansley et al. |
| 8,961,389 B2 | 2/2015 | Zilbershlag |
| 9,002,468 B2 | 4/2015 | Shea et al. |
| 9,002,469 B2 | 4/2015 | D'Ambrosio |
| 9,071,182 B2 | 6/2015 | Yoshida et al. |
| 9,220,826 B2 | 12/2015 | D'Ambrosio |
| 9,283,314 B2 | 3/2016 | Prasad et al. |
| 9,381,286 B2 | 7/2016 | Spence et al. |
| 9,440,013 B2 | 9/2016 | Dowling et al. |
| 9,456,898 B2 | 10/2016 | Barnes et al. |
| 9,486,566 B2 | 11/2016 | Siess |
| 9,492,600 B2 | 11/2016 | Strueber et al. |
| 9,539,094 B2 | 1/2017 | Dale et al. |
| 9,561,362 B2 | 2/2017 | Malinowski |
| 9,569,985 B2 | 2/2017 | Alkhatib et al. |
| 9,592,397 B2 | 3/2017 | Hansen et al. |
| 9,603,984 B2 | 3/2017 | Romero et al. |
| 9,616,107 B2 | 4/2017 | VanAntwerp et al. |
| 9,713,701 B2 | 7/2017 | Sarkar et al. |
| 9,717,831 B2 | 8/2017 | Schuermann |
| 9,724,083 B2 | 8/2017 | Quadri et al. |
| 9,800,172 B1 | 10/2017 | Leabman |
| 9,833,314 B2 | 12/2017 | Corbett |
| 9,833,611 B2 | 12/2017 | Govea et al. |
| 9,848,899 B2 | 12/2017 | Sliwa et al. |
| 9,974,894 B2 | 5/2018 | Morello |
| 10,143,571 B2 | 12/2018 | Spence et al. |
| 10,463,508 B2 | 11/2019 | Spence et al. |
| 10,732,583 B2 | 8/2020 | Rudser |
| 10,944,293 B2 | 3/2021 | Nakao |
| 11,000,282 B2 | 5/2021 | Schuelke et al. |
| 11,056,878 B2 | 7/2021 | Gao et al. |
| 11,065,437 B2 | 7/2021 | Aber et al. |
| 11,103,715 B2 | 8/2021 | Fort |
| 11,110,265 B2 | 9/2021 | Johnson |
| 11,179,559 B2 | 11/2021 | Hansen |
| 11,224,737 B2 | 1/2022 | Petersen et al. |
| 11,291,826 B2 | 4/2022 | Tuval et al. |
| 11,316,371 B1 | 4/2022 | Partovi et al. |
| 11,317,988 B2 | 5/2022 | Hansen et al. |
| 11,344,717 B2 | 5/2022 | Kallenbach et al. |
| 11,351,359 B2 | 6/2022 | Clifton et al. |
| 11,351,360 B2 | 6/2022 | Rudser et al. |
| 11,368,081 B2 | 6/2022 | Vogt et al. |
| 11,369,785 B2 | 6/2022 | Callaway et al. |
| 11,369,786 B2 | 6/2022 | Menon et al. |
| 11,389,641 B2 | 7/2022 | Nguyen et al. |
| 11,406,483 B2 | 8/2022 | Wirbisky et al. |
| 11,406,520 B2 | 8/2022 | Lam |
| 11,406,802 B2 | 8/2022 | DeGraaf et al. |
| 11,413,443 B2 | 8/2022 | Hodges et al. |
| 11,413,444 B2 | 8/2022 | Nix et al. |
| 11,439,806 B2 | 9/2022 | Kimball et al. |

(56) References Cited

U.S. PATENT DOCUMENTS

| | | |
|---|---|---|
| 11,471,692 B2 | 10/2022 | Aghassian et al. |
| 11,497,906 B2 | 11/2022 | Grace et al. |
| 11,517,737 B2 | 12/2022 | Struthers et al. |
| 11,517,738 B2 | 12/2022 | Wisniewski |
| 11,517,740 B2 | 12/2022 | Agarwa et al. |
| 11,529,508 B2 | 12/2022 | Jablonsk et al. |
| 11,583,671 B2 | 2/2023 | Nguyen et al. |
| 11,596,727 B2 | 3/2023 | Siess et al. |
| 11,602,624 B2 | 3/2023 | Siess et al. |
| 11,682,924 B2 | 6/2023 | Hansen et al. |
| 11,689,057 B2 | 6/2023 | Hansen |
| 11,699,551 B2 | 7/2023 | Diekhans et al. |
| 11,745,005 B2 | 9/2023 | Delgado, III |
| 11,752,354 B2 | 9/2023 | Stotz et al. |
| 11,804,767 B2 | 10/2023 | Vogt et al. |
| 11,881,721 B2 | 1/2024 | Araujo et al. |
| 2001/0016686 A1 | 8/2001 | Okada et al. |
| 2002/0177324 A1 | 11/2002 | Metzler |
| 2003/0040765 A1 | 2/2003 | Breznock |
| 2003/0125766 A1 | 7/2003 | Ding |
| 2003/0130581 A1 | 7/2003 | Salo et al. |
| 2004/0167410 A1 | 8/2004 | Hettrick |
| 2005/0006083 A1 | 1/2005 | Chen et al. |
| 2005/0107658 A1 | 5/2005 | Brockway |
| 2005/0107847 A1 | 5/2005 | Gruber et al. |
| 2006/0004423 A1 | 1/2006 | Boveja et al. |
| 2006/0190036 A1* | 8/2006 | Wendel ............ A61B 17/0057 606/213 |
| 2006/0196277 A1 | 9/2006 | Allen et al. |
| 2007/0129767 A1 | 6/2007 | Wahlstrand |
| 2007/0282209 A1 | 12/2007 | Lui et al. |
| 2008/0015481 A1 | 1/2008 | Bergin et al. |
| 2008/0079392 A1 | 4/2008 | Baarman et al. |
| 2008/0082005 A1 | 4/2008 | Stern et al. |
| 2008/0211455 A1 | 9/2008 | Park et al. |
| 2008/0266922 A1 | 10/2008 | Mumtaz et al. |
| 2009/0010462 A1 | 1/2009 | Ekchian et al. |
| 2009/0024042 A1 | 1/2009 | Nunez et al. |
| 2009/0134711 A1 | 5/2009 | Issa et al. |
| 2009/0198307 A1 | 8/2009 | Mi et al. |
| 2009/0198312 A1 | 8/2009 | Barker |
| 2009/0276016 A1 | 11/2009 | Phillips et al. |
| 2009/0312650 A1 | 12/2009 | Maile et al. |
| 2010/0191035 A1 | 7/2010 | Kang et al. |
| 2010/0219967 A1 | 9/2010 | Kaufmann |
| 2010/0280568 A1 | 11/2010 | Bulkes et al. |
| 2010/0312310 A1 | 12/2010 | Meskens |
| 2010/0331918 A1 | 12/2010 | Digiore et al. |
| 2011/0071336 A1 | 3/2011 | Yomtov |
| 2011/0137394 A1 | 6/2011 | Lunsford et al. |
| 2011/0224720 A1 | 9/2011 | Kassab et al. |
| 2012/0022645 A1 | 1/2012 | Burke |
| 2012/0050931 A1 | 3/2012 | Terry et al. |
| 2012/0112543 A1 | 5/2012 | van Wageningen et al. |
| 2012/0158074 A1 | 6/2012 | Hall |
| 2012/0212178 A1 | 8/2012 | Kim |
| 2012/0235633 A1 | 9/2012 | Kesler et al. |
| 2013/0069651 A1 | 3/2013 | Lumiani |
| 2013/0099585 A1 | 4/2013 | Von Novak et al. |
| 2013/0116575 A1 | 5/2013 | Mickle et al. |
| 2013/0303970 A1 | 11/2013 | Keenan et al. |
| 2014/0012282 A1* | 1/2014 | Fritsch .................. A61F 11/00 623/10 |
| 2014/0039587 A1 | 2/2014 | Romero |
| 2014/0063666 A1 | 3/2014 | Kallal et al. |
| 2014/0094645 A1 | 4/2014 | Lafontaine et al. |
| 2014/0104898 A1 | 4/2014 | Yeo et al. |
| 2014/0107754 A1 | 4/2014 | Fuhs et al. |
| 2014/0135884 A1 | 5/2014 | Tockman et al. |
| 2014/0194058 A1 | 7/2014 | Lee et al. |
| 2014/0233184 A1 | 8/2014 | Thompson et al. |
| 2014/0249603 A1 | 9/2014 | Yan et al. |
| 2014/0265620 A1 | 9/2014 | Hoarau et al. |
| 2015/0008755 A1 | 1/2015 | Sone |
| 2015/0028805 A1 | 1/2015 | Dearden et al. |
| 2015/0090372 A1 | 4/2015 | Branagan et al. |
| 2015/0196076 A1 | 7/2015 | Billingslea |
| 2015/0290372 A1 | 10/2015 | Muller et al. |
| 2015/0290373 A1 | 10/2015 | Rudser et al. |
| 2015/0333532 A1 | 11/2015 | Han et al. |
| 2015/0380972 A1 | 12/2015 | Fort |
| 2016/0022889 A1 | 1/2016 | Bluvshtein et al. |
| 2016/0067395 A1 | 3/2016 | Jimenez et al. |
| 2016/0081680 A1 | 3/2016 | Taylor |
| 2016/0087558 A1 | 3/2016 | Yamamoto |
| 2016/0095968 A1 | 4/2016 | Rudser |
| 2016/0175501 A1 | 6/2016 | Schuermann |
| 2016/0268846 A1 | 9/2016 | Akuzawa et al. |
| 2016/0271309 A1 | 9/2016 | Throckmorton et al. |
| 2016/0331980 A1 | 11/2016 | Strommer et al. |
| 2016/0344302 A1 | 11/2016 | Inoue |
| 2017/0047781 A1 | 2/2017 | Stanislawski et al. |
| 2017/0070082 A1 | 3/2017 | Zheng et al. |
| 2017/0136164 A1 | 5/2017 | Yeatts |
| 2017/0143977 A1 | 5/2017 | Kaib et al. |
| 2017/0202575 A1 | 7/2017 | Stanfield et al. |
| 2017/0203104 A1 | 7/2017 | Nageri et al. |
| 2017/0231717 A1 | 8/2017 | Forsell |
| 2017/0271919 A1 | 9/2017 | Von Novak, III et al. |
| 2017/0275799 A1 | 9/2017 | Chen |
| 2017/0288448 A1 | 10/2017 | Kranz et al. |
| 2017/0303375 A1 | 10/2017 | Woodhead |
| 2017/0353053 A1 | 12/2017 | Muratov |
| 2017/0354812 A1 | 12/2017 | Callaghan et al. |
| 2018/0078329 A1 | 3/2018 | Hansen et al. |
| 2018/0194236 A1 | 7/2018 | Elshaer et al. |
| 2018/0207336 A1 | 7/2018 | Solem |
| 2018/0256796 A1 | 9/2018 | Hansen |
| 2018/0256800 A1 | 9/2018 | Conyers et al. |
| 2018/0280708 A1 | 10/2018 | Escalona et al. |
| 2018/0316209 A1 | 11/2018 | Gliner |
| 2019/0004037 A1 | 1/2019 | Zhang et al. |
| 2019/0060543 A1 | 2/2019 | Khanal et al. |
| 2019/0068004 A1 | 2/2019 | Louis |
| 2019/0097447 A1 | 3/2019 | Partovi |
| 2019/0175808 A1 | 6/2019 | Zilbershlag et al. |
| 2019/0222064 A1 | 7/2019 | Du et al. |
| 2019/0344000 A1 | 11/2019 | Kushwaha et al. |
| 2019/0351120 A1 | 11/2019 | Kushwaha et al. |
| 2019/0393735 A1 | 12/2019 | Lee et al. |
| 2020/0054806 A1 | 2/2020 | Sun |
| 2020/0139032 A1 | 5/2020 | Bryson et al. |
| 2020/0227954 A1 | 7/2020 | Ding et al. |
| 2020/0350812 A1 | 11/2020 | Vogt et al. |
| 2021/0052793 A1 | 2/2021 | Struthers et al. |
| 2021/0057804 A1 | 2/2021 | Wenning |
| 2021/0143688 A1 | 5/2021 | Agrawal et al. |
| 2021/0290931 A1 | 9/2021 | Baumbach |
| 2021/0336484 A1 | 10/2021 | Araujo et al. |
| 2021/0379360 A1 | 12/2021 | Schellenberg |
| 2021/0386990 A1 | 12/2021 | Stotz et al. |
| 2021/0393944 A1 | 12/2021 | Wenning |
| 2021/0399582 A1 | 12/2021 | Araujo et al. |
| 2022/0080184 A1 | 3/2022 | Clifton et al. |
| 2022/0080185 A1 | 3/2022 | Clifton et al. |
| 2022/0320901 A1 | 10/2022 | Araujo et al. |
| 2023/0191141 A1 | 6/2023 | Wenning et al. |
| 2023/0352236 A1 | 11/2023 | Diekhans et al. |
| 2023/0381526 A1 | 11/2023 | Stotz et al. |

FOREIGN PATENT DOCUMENTS

| | | |
|---|---|---|
| CN | 103942511 | 7/2014 |
| CN | 104274873 | 1/2015 |
| CN | 104888293 | 3/2017 |
| CN | 106776441 | 5/2017 |
| DE | 103 02 550 | 8/2004 |
| DE | 10 2012 200 912 | 7/2013 |
| DE | 11 2012 005 944 | 12/2014 |
| DE | 10 2016 106 683 | 10/2016 |
| DE | 10 2018 206 758 | 11/2019 |
| EP | 0 930 086 | 7/1999 |
| EP | 2 454 799 | 5/2012 |
| EP | 2 752 209 | 7/2014 |

(56) References Cited

FOREIGN PATENT DOCUMENTS

| | | |
|---|---|---|
| EP | 2 782 210 | 9/2014 |
| EP | 2 859 911 | 4/2015 |
| EP | 2 966 753 | 1/2016 |
| EP | 2 709 689 | 4/2017 |
| EP | 3 220 505 | 9/2017 |
| EP | 3 357 523 | 1/2021 |
| EP | 3 423 126 | 2/2021 |
| EP | 3 490 628 | 2/2021 |
| EP | 3 198 677 | 3/2021 |
| EP | 3 248 647 | 3/2021 |
| EP | 3 436 106 | 3/2021 |
| EP | 3 509 661 | 3/2021 |
| EP | 3 528 863 | 3/2021 |
| EP | 3 436 105 | 4/2021 |
| EP | 3 116 407 | 5/2021 |
| EP | 3 131 600 | 6/2021 |
| EP | 2 608 731 | 7/2021 |
| EP | 2 599 510 | 10/2021 |
| EP | 3 077 018 | 10/2021 |
| EP | 3 485 936 | 10/2021 |
| EP | 3 539 613 | 2/2022 |
| EP | 2 858 718 | 3/2022 |
| EP | 3 624 867 | 3/2022 |
| EP | 3 755 237 | 4/2022 |
| EP | 3 497 775 | 7/2022 |
| EP | 3 711 788 | 8/2022 |
| EP | 2 654 883 | 9/2022 |
| EP | 3 485 819 | 9/2022 |
| EP | 3 600 477 | 10/2022 |
| EP | 3 808 408 | 11/2022 |
| EP | 3 858 422 | 11/2022 |
| EP | 2 892 583 | 1/2023 |
| EP | 3 597 231 | 1/2023 |
| EP | 3 856 275 | 1/2023 |
| EP | 3 003 420 | 2/2023 |
| EP | 3 946 511 | 4/2023 |
| EP | 3 826 104 | 5/2023 |
| JP | H11-178249 | 7/1999 |
| JP | 2013-013216 | 1/2013 |
| JP | 2018-046708 | 3/2018 |
| KR | 10-1185112 | 9/2012 |
| WO | WO 2008/106103 | 9/2008 |
| WO | WO 2009/023905 | 2/2009 |
| WO | WO 2009/029977 | 3/2009 |
| WO | WO 2010/042054 | 4/2010 |
| WO | WO 2011/007300 | 1/2011 |
| WO | WO 2012/147061 | 11/2012 |
| WO | WO 2013/164831 | 11/2013 |
| WO | WO 2015/152732 | 10/2015 |
| WO | WO 2017/021846 | 2/2017 |
| WO | WO 2017/060257 | 4/2017 |
| WO | WO 2017/066257 | 4/2017 |
| WO | WO 2017/089440 | 6/2017 |
| WO | WO 2017/118738 | 7/2017 |
| WO | WO 2017/165372 | 9/2017 |
| WO | WO 2017/218349 | 12/2017 |
| WO | WO 2018/033799 | 2/2018 |
| WO | WO 2018/100192 | 6/2018 |
| WO | WO 2019/025258 | 2/2019 |
| WO | WO 2019/025259 | 2/2019 |
| WO | WO 2019/025260 | 2/2019 |
| WO | WO 2019/101786 | 5/2019 |
| WO | WO 2019/145253 | 8/2019 |
| WO | WO 2019/158996 | 8/2019 |
| WO | WO 2019/183247 | 9/2019 |
| WO | WO 2019/185511 | 10/2019 |
| WO | WO 2019/185512 | 10/2019 |
| WO | WO 2019/211400 | 11/2019 |
| WO | WO 2019/211405 | 11/2019 |
| WO | WO 2019/211410 | 11/2019 |
| WO | WO 2019/211413 | 11/2019 |
| WO | WO 2019/211414 | 11/2019 |
| WO | WO 2019/211415 | 11/2019 |
| WO | WO 2019/211416 | 11/2019 |
| WO | WO 2019/229224 | 12/2019 |
| WO | WO 2019/234151 | 12/2019 |
| WO | WO 2019/241556 | 12/2019 |
| WO | WO 2019/244031 | 12/2019 |
| WO | WO 2020/089429 | 5/2020 |
| WO | WO 2023/076869 | 5/2023 |

OTHER PUBLICATIONS

Leguy et al., "Assessment of Blood vol. Flow in Slightly Curved Arteries from a Single Velocity Profile", Journal of Biomechanics, 2009, pp. 1664-1672.

Murali, Akila, "Design of Inductive Coils for Wireless Power Transfer to Pediatric Implants", A graduate project submitted in partial fulfillment of the requirements For the degree of Master of Science in Electrical Engineering, California State University, Northridge, May 2018, pp. 37.

Sinha et al., "Effect of Mechanical Assistance of the Systemic Ventricle in Single Ventricle Circulation with Cavopulmonary Connection", The Journal of Thoracic and Cardiovascular Surgery, Apr. 2014, vol. 147, No. 4, pp. 1271-1275.

Vieli, A., "Doppler Flow Determination", BJA: British Journal of Anaesthesia, 1988, vol. 60, pp. 107S-112S.

* cited by examiner

METHOD FOR PUNCHING A LUMEN AND IMPLANTING AN IMPLANT DEVICE

CROSS-REFERENCE TO RELATED APPLICATIONS

This application is a continuation of U.S. patent application Ser. No. 15/613,409, filed Jun. 5, 2017, which claims priority under 35 U.S.C. § 119 to German Patent Application No. DE 10 2016 209 871.3, filed Jun. 6, 2016, the entire disclosure of each of which is hereby incorporated by reference herein in its entirety.

BACKGROUND

Field

The approach is directed to a device or a method of the type described in the disclosure.

Description of the Related Art

In order to open a liquid- and/or air-filled lumen, which is in the form of a blood vessel in this case, by way of example, but which can also be a stomach, an intestine, or a trachea, it is possible to manually cut into the blood vessel using a scalpel. A piece of the blood vessel can then be removed in various ways. The blood vessel can also be merely expanded and subsequently sutured together again. When the blood vessel is punched, it is necessary to at least partially clamp the blood vessel and/or connect the patient to a heart-lung machine. In order to make it possible, for example, to route a power cable, which is connected to a VAD pump, out of the aorta, it would be necessary to punch the ascending aorta and subsequently implant a wire mesh into the aorta in order to hold the aorta open.

SUMMARY

Against this background, the approach presented here provides a punching device for punching a lumen and implanting an implant device, and a method for punching a lumen and implanting an implant device according to the disclosure. Due to the measures described in the dependent claims, advantageous refinements and improvements of the punching device described in the disclosure are possible.

A punching device for punching a lumen and implanting an implant device is provided. In this case, the lumen can be, for example, a blood vessel, a stomach, an intestine, or a trachea. The punching device comprises at least the implant device, an implantation device, a closure device, and an actuation device. The implant device is designed for punching the lumen and for being implanted into the lumen. The implantation device is coupled to the implant device and is designed for punching the implant device into the lumen by way of a forward motion and for effectuating the implantation of the implant device into the punched lumen by way of a return motion of at least one part of the implantation device. The closure device is coupled at least to the implantation device and is designed in such a way that, in an open state, it releases a restoring force for effectuating the forward motion of the implantation device, in order to punch the lumen. In a closed state, the closure device can be designed for holding the implantation device, including the coupled implant device, in the punching device. The actuation device is coupled to the closure device and is designed for bringing about the opened state of the closure device and effectuating the return motion of the implantation device in response to at least one actuation. The actuation device can also be designed for bringing about the opened state of the closure device in response to a first actuation and for effectuating the return motion of the implantation device in response to a second actuation.

A punching device presented here makes it possible to punch a lumen and implant an implantation device by actuating a single actuation device. The actuations can be effectuated, for example, by a surgeon by moving a single operating element, for example in the form of a rotary knob or a push-button. The operating element can be part of the actuation device or can be coupled to the actuation device. In this case, the implant device advantageously performs the function of the punch and of the implant. Therefore, an additional punching device for punching the lumen is not necessary. In this way, by means of the above-described forward motion of the implantation device, the lumen is punched by the implant device and the implant device is already positioned at the point in the lumen where it is to be implanted. In order to perform the implantation, all that is necessary is to then withdraw the implantation device. The punching device presented here can punch the lumen and implant the implant device in only two simple motions, namely the forward motion and the return motion of the implantation device. The punching device can comprise a housing which accommodates the implant device, the implantation device, the closure device, and the actuation device. The closure device can be designed as a plug-and-socket connector which can comprise a spring for providing the restoring force or can be coupled to such a spring. The plug-and-socket connector and/or the spring can be preloaded, or can have been already preloaded, during the assembly of the punching device. According to one embodiment, the punching device has a size and a shape which make it possible for a surgeon to handle the punching device. For example, the punching device has a length of less than 30 cm and has a width or height of less than 10 cm. According to one embodiment, the punching device is designed as a device for single use.

For the purpose of guiding and surrounding the implant device, the implantation device can comprise at least one inner sleeve for guiding the implant device and an outer sleeve for surrounding the implant device, wherein the outer sleeve can be designed for surrounding the inner sleeve in an at least partially linearly movable manner. In this way, the inner sleeve and the outer sleeve can be movable separately from each other. When the outer sleeve is designed for carrying out the return motion in order to effectuate the implantation of the implant device into the punched lumen, the inner sleeve can be designed, for example, to stand still during the return motion of the outer sleeve. In this way, the implant device can be held by the inner sleeve at the intended point in the lumen, while the return motion of the outer sleeve effectuates the implantation at this point.

This can be possible, for example, when the implant device comprises a mesh having shape memory. The mesh having shape memory can be, for example, a wire mesh in this case, which is made at least partially of a shape memory alloy. The mesh having shape memory can be disposed, for example, in such a way that it is compressed by the surrounding outer sleeve and can expand to a predetermined size during implantation in the lumen, in order to ensure a rapidly sealing connection between the lumen and the implant device.

The implant device can also be designed as a wire mesh which is multifunctional and, for example, comprises a sealing element. For example, the implant device consists of a wire mesh, on the one hand and, on the other hand, is encapsulated in a sealing material, for example. Additionally or alternatively, the implant device can be designed in such a way that, in the implanted state, it holds the blood vessel open.

It is also advantageous when the punching device comprises an opening device which is coupled to the implantation device, wherein the opening device can comprise at least one opening unit which can be designed for opening the lumen before the punching, in response to the forward motion. This opening unit can be designed, for example, as a pointed tip which punctures the lumen, in a punctiform and, therefore, gentle manner, before the punching. When the opening unit also comprises a barb, a lumen section of the lumen, which is to be punched out, can be advantageously captively fixed on the barb during the opening of the lumen. When the opening device also executes a return motion in response to the return motion of the implantation device, the punched lumen section can be advantageously reliably removed from the lumen.

In order to save installation space, it is possible according to one embodiment to dispose the implant device and the implantation device ideally on one axis. The opening device can be accommodated, in this case, at least partially by the implantation device and/or the implant device in order to also allow for opening on the same axis of motion.

According to one embodiment, the closure device can comprise at least one bayonet lock including a rotatable rotary element and a rotatable and linearly movable linear unit, wherein, in order to provide the restoring force, the closure device can comprise at least one spring which can be loaded in a closed state of the bayonet lock. A plug-and-socket connector such as a bayonet lock can be reliably closed and easily mechanically opened. For this purpose, the bayonet lock can be advantageously designed to be transferred from the closed state into the opened state by means of a rotation of the rotary element, wherein the linear unit can be designed in such a way that, when the bayonet lock is transferred into the opened state, the linear unit executes a linear opening motion in the direction of an outlet opening of the punching device in order to effectuate the forward motion of the implantation device coupled to the linear unit. When the implantation device, together with the implant device, is coupled to the linear unit, the implantation device and the implant device can therefore execute the forward motion in response to the linear opening motion of the linear unit.

The outlet opening is an opening in the housing of the punching device, through which the implant device and the implantation device at least partially emerge from the housing during punching and implantation.

In order to couple the implantation device to the closure device, at least one sleeve of the implantation device can comprise at least one pin to be accommodated in at least one guide groove of the linear unit and/or the linear unit comprises at least the guide groove for accommodating the pin of the sleeve. The guide groove and the pin can be designed in such a way in this case that, in a coupled state, they effectuate the return motion of the implantation device in response to the actuation of the actuation device after the lumen has been punched. It is advantageous, in particular, when the inner sleeve and the outer sleeve each comprise such a pin, which are accommodated in different guide grooves in the linear unit. By way of a different embodiment of the guide grooves, the inner sleeve and the outer sleeve can be guidable in the guide grooves in different ways and, therefore can be moved in different ways. The opening device can also comprise such a pin which can be accommodated in one further groove in the linear unit in order to make the opening device movable, for example, in response to the forward motion of the linear unit.

According to one embodiment, the punching device can comprise a rotary knob or a push-button which is designed for effectuating the at least one actuation of the actuation device in response to a rotary actuation or a push actuation. Advantageously, the opened state of the closure device can be brought about first, for example, by continuing the rotary actuation and, subsequent thereto, the return motion of the implantation device can be executed. For this purpose, the linear unit can be designed to be rotatable in order to be able to continue the rotary actuation of the rotary knob. In this way, the lumen can be punched and the implant device can be implanted by means of the punching device simply by way of a rotary actuation or a push actuation. The rotary or push actuation can take place in this case by means of an operator of the punching device, for example, by a surgeon or an operating surgeon.

A method for punching a lumen and implanting an implant device comprises at least the following steps:

bringing about an opened state of a closure device in order to release a restoring force for effectuating a forward motion of an implantation device coupled to the closure device, in order to punch the lumen by means of the implant device coupled to the implantation device, wherein the opened state of the closure device is brought about by means of at least one actuation of an actuation device coupled to the closure device; and executing a return motion of the implantation device in order to effectuate the implantation of the implant device, which is coupled to the implantation device, into the punched lumen, wherein the return motion of the implantation device is executed by means of the at least one actuation of the actuation device.

This method can be carried out using the aforementioned punching device. The above-described advantages of the punching device can also be implemented by means of such a method.

BRIEF DESCRIPTION OF THE DRAWINGS

Exemplary embodiments of the approach presented here are represented in the drawings and are described in greater detail in the following description. In the drawings.

DETAILED DESCRIPTION

Figure 1:
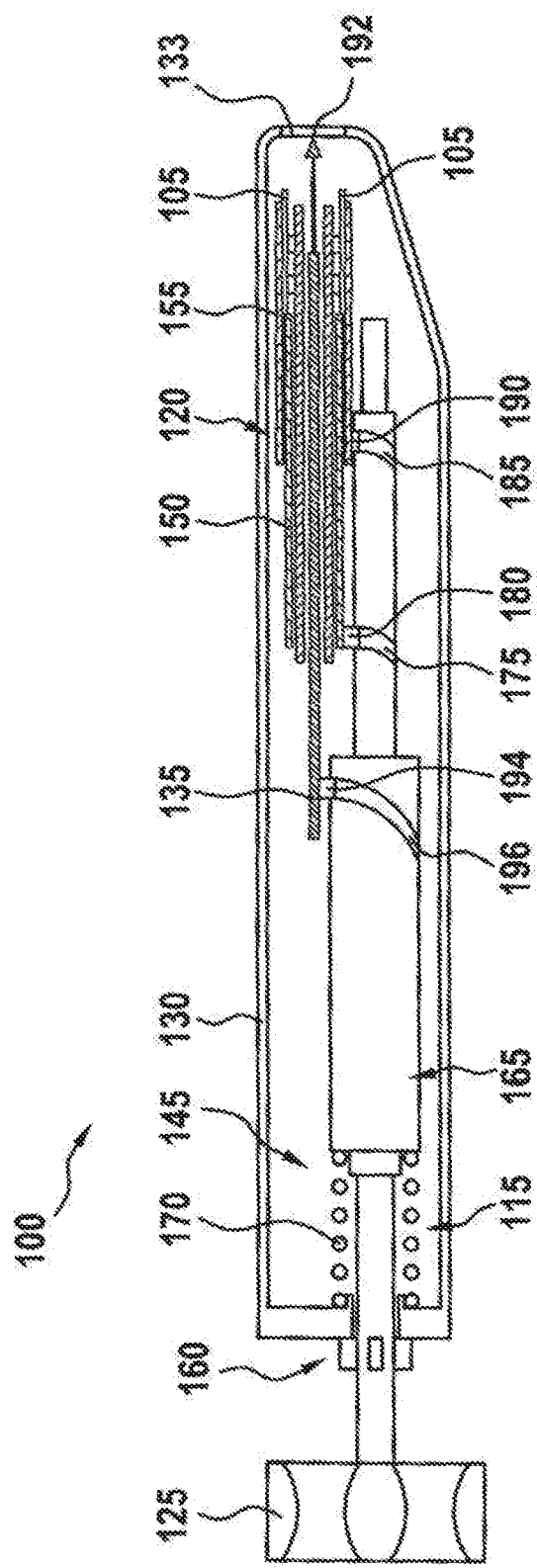
FIG. 1 shows a cross-section of a side view of a punching device for punching a lumen and implanting an implant device according to one exemplary embodiment.

In the following description of favorable exemplary embodiments of the present approach, the same or similar reference characters are used for the elements that are represented in the various figures and act in a similar manner, wherein a description of these elements is not repeated.

FIG. 1 shows a cross-section of a side view of a punching device 100 for punching a lumen and implanting an implant device 105 according to one exemplary embodiment. According to this exemplary embodiment, the lumen is in the form of a blood vessel. According to one alternative exemplary embodiment, the lumen can also be a stomach, an intestine, or a trachea.

The punching device 100 comprises the implant device 105, a closure device 115, an implantation device 120, and an actuation device 125.

Optionally, the punching device 100 also comprises a housing 130, in which the aforementioned devices 105, 115, 120, except for the actuation device 125, are accommodated for protection. The housing 130 comprises, at one end of the punching device 100, an outlet opening 133, through which the implant device 105 and the implantation device 120 at least partially emerge from the punching device 100 during punching. Optionally, the punching device 100 also comprises an opening device 135 for opening the blood vessel before the punching.

The implant device 105 is designed for punching the blood vessel and, according to this exemplary embodiment, also for holding the blood vessel open in a state in which the implant device has been implanted into the blood vessel. For this purpose, the implant device 105 according to this exemplary embodiment comprises a wire mesh having shape memory, whereby the implant device 105 is designed to sealingly expand in the blood vessel when the implant device is in the implanted state.

The implantation device 120 is coupled to the implant device 105 and is designed for punching the implant device 105 into the blood vessel by way of a forward motion and for effectuating the implantation of the implant device 105 into the punched blood vessel by way of a return motion of at least one part of the implantation device 120.

The closure device 115 is coupled to the implantation device 120 and is designed in such a way that, in an open state, it releases a restoring force for effectuating the forward motion of the implantation device 120, in order to punch the blood vessel. According to this exemplary embodiment, the closure device 115 is in a closed state 145 in which the closure device 115 is designed for holding the implantation device 120, including the coupled implant device 105, in the housing 130 of the punching device 100.

The actuation device 125 is coupled to the closure device 115 and is designed for bringing about the opened state of the closure device 115 in response to a first actuation and effectuating the return motion of the implantation device 120 in response to a second actuation. According to one alternative exemplary embodiment, the forward motion, the opened state, and the linear motion can also be executed/brought about in response to a single actuation of the actuation device 125. According to this exemplary embodiment, the actuation device 125 is designed as a rotary knob which is designed for effectuating, in response to a rotary actuation, the first actuation of the actuation device 125 and then the second actuation of the actuation device. According to one alternative exemplary embodiment, the actuation device 125 comprises, in addition or as an alternative to the rotary knob, a push-button which is designed for effectuating the above-described actuations of the actuation device 125 in response to a push actuation.

According to this exemplary embodiment, the implantation device 120 comprises an inner sleeve 150 and an outer sleeve 155. The inner sleeve 150 is partially accommodated by the outer sleeve 155, wherein the outer sleeve 155 surrounds the inner sleeve 150 in a linearly movable manner. The inner sleeve 150 is designed for guiding the implant device 105. The outer sleeve 155 is designed for surrounding the implant device 105 and holding it in a compressed state before the return motion is executed; for this purpose, the implant device 105 according to this exemplary embodiment is completely accommodated in the outer sleeve 155. According to this exemplary embodiment, the implant device 105 and the implantation device 120 are disposed on one axis.

According to this exemplary embodiment, the outer sleeve 155 is designed for executing the return motion for effectuating the implantation of the implant device 105 into the punched blood vessel, while the inner sleeve 150 stands still. According to this exemplary embodiment, the inner sleeve 150 is designed for executing a return motion out of the blood vessel in response to a third actuation of the actuation device 125, after the implant device 105 has been implanted by means of the return motion of the outer sleeve 155.

According to this exemplary embodiment, the closure device 115 is designed as a plug-and-socket connector in the form of a bayonet lock which comprises a rotatable rotary element 160 and a rotatable and linearly movable linear unit 165. According to this exemplary embodiment, the linear unit 165 is coupled to the implantation device 120 and is rotatable in response to the actuation. In order to provide the restoring force, the closure device 115 according to this exemplary embodiment comprises a spring 170 which is loaded in the closed state 145 of the bayonet lock. The bayonet lock is designed to be transferred from the closed state 145 into the opened state by means of a rotation of the rotary element 160, wherein the linear unit 165 is designed in such a way that, when the bayonet lock is transferred into the opened state, the linear unit executes a linear opening motion in the direction of the outlet opening 133 of the punching device 100 in order to effectuate the forward motion of the implantation device 120 coupled to the linear unit 165.

For the purpose of coupling the closure device 115 to the implantation device 120, the linear unit 165 according to this exemplary embodiment comprises an inner sleeve groove 175 for accommodating an inner sleeve cam 180 of the inner sleeve 150 and an outer sleeve groove 185 for accommodating an outer sleeve cam 190 of the outer sleeve 155. The inner sleeve groove 175 and the outer sleeve groove 185 are designed in such a way in this case that, in a coupled state with the inner sleeve cam 180 and the outer sleeve cam 190, the return motion of the outer sleeve 155 is effectuated in response to the second actuation of the actuation device 125 and, subsequent thereto, the return motion of the inner sleeve 150.

The opening device 135 comprises an opening unit 192 which is designed for opening the blood vessel before the punching, in response to the forward motion of the implantation device 120. For this purpose, the opening device 135 according to this exemplary embodiment is coupled to the implantation device 120 and, in addition, is accommodated in the implantation device 120. The opening device 135 comprises an opening device cam 194 which is accommodated by an opening device groove 196 of the linear unit 165. The opening unit 192 comprises a barb which is designed for captively fixing a blood vessel section of the blood vessel to be punched, during the opening of the blood vessel.

Details which have already been described with reference to FIG. 1 are commented on again, more precisely, in the following.

As technology matures, machines will be implanted in the bodies of humans to an increasing extent, and so there is a need for a device which punches a hole into a blood vessel, which was referred to previously as a blood vessel, in a minimally invasive way and implants a wire mesh such as the implant device 105 into the blood vessel, the wire mesh holding this hole open. Such a device is the punching device 100 presented here. Cables can be routed out of the blood vessels or slid into the blood vessels, for example, through the hole punched by means of the punching device 100. One example of such a machine is the mechanical ventricular assist device (VAD). These machines carry out their function in the body. In order to ensure a power supply to these machines in the blood vessels, it will become necessary increasingly frequently in the future to route power cables or general supply cables through blood vessel walls.

The punching device 100 presented here is designed for punching—on the pulsating blood vessel, in particular on the beating aorta, without clamping the aorta—a hole into the aorta and introducing an implant device 105, through which a supply cable can be routed. After the supply cable is routed through, the implantation is tightly sealed.

The clamping of the aorta can be advantageously dispensed with in this case, which has considerable advantages for the patient, since the clamping of blood vessels can lead to the formation of thrombi, for example. If these thrombi become detached and travel, for example, to a constriction in the brain, this can result in a cerebrovascular accident.

In addition, the patient advantageously does not need to be connected to a heart-lung machine during the punching of the blood vessel and implantation of the implant device 105 by means of the punching device 100. The heart-lung machine is an invasive method that surgeons like to avoid if at all possible.

In addition, when the punching device 100 presented here is utilized, for example, on the aorta, only a partial sternotomy is necessary. Devices for implanting bypasses at the aorta, in the case of which the aorta is punched and an anastomosis is established between the aorta and a vein, which had been previously removed, cannot be used for the application described. An anastomosis refers to a natural or artificial connection between blood vessels. These devices are too large and require a complete sternotomy. The approach presented here, however, takes place less invasively, i.e., only a partial sternotomy is necessary in the case of an application of the punching device 100 at the aorta.

As described above, the punching device 100 presented here makes it possible to carry out the described type of surgical procedures less invasively and with less risk. Due to the use of the punching device 100, it is not necessary to clamp the blood vessels or utilize a heart-lung machine. In addition, the operation can be carried out using a partial sternotomy. Given that there is no need to suture the blood vessels, the duration of the operation is reduced and the handling is simplified. Instead of cutting the blood vessel open, punching a hole, inserting a stent, and suturing in order to seal, the surgeon can simply turn the rotary knob 125 or, according to one alternative exemplary embodiment, press on the push-button.

The punching device 100 integrates, in short, the functions of punching the blood vessel, removing the punched-out tissue, and implanting an implant device 105 which holds the hole open with a defined inner diameter.

In this case, the punching device 100 is protected against slipping during the process. The implant device 105 seals toward the outside and, after the cable has been routed through, it also seals toward the inside. The punching device 100 is used only one time. The implant device 105 remains implanted in the body for the same length of time as the cable which is routed through the hole that is produced. The punching device 100 functions purely mechanically. The required introduction of force takes place either by preloading the spring 170 or, according to one alternative exemplary embodiment, by means of the muscular force of the surgeon.

Represented here is a cross-section of a side view of the punching device 100 in the starting state with only one housing half of the housing 130. In one operating step, the punching device 100 can punch a hole into the blood vessel, remove the punched-out tissue, and implant a wire mesh which seals toward the outside. Initially, the punching device 100 is pressed onto the blood vessel to be worked on. A device, which is not described in further detail and which can be coupled, for example, to the punching device 100, prevents the punching device 100 from slipping. A next operating step is disengaging the securing mechanism. This takes place via an axial motion of a securing button of the punching device 100. Next, the rotary knob 125 is rotated through one to two revolutions in all. As a result, the linear unit 165 is rotated, on the surface of which guide grooves in the form of the inner sleeve groove 175 presented here, the outer sleeve groove 185, and the opening device groove 196 extend. The linear unit 165 can also be referred to as a guide shaft. These guide grooves make it possible for different tools in the form of the inner sleeve 150 and the outer sleeve 155 of the implantation device 120 and the opening device 135 to move relative to one another using only one operating element. The tools required for implementing the desired application each comprise a pin in the form of the inner sleeve cam 180, the outer sleeve cam 190, and the opening device cam 194, for example made of metal, each extending in a groove in the linear unit 165 provided separately therefor. The aforementioned securing mechanism also functions in this way. It also includes a securing pin which extends in a securing groove. Before the securing mechanism of the punching device 100 is disengaged, the securing pin is located in a small recess on the linear unit 165, whereby the rotary motion of the linear unit 165 is blocked. The individual tools are guided by guide rails which are disposed on the inner housing wall of the housing halves of the housing 130. The guide rails are disposed close to a plane of the largest force transmission in this case. This means that the guide rails of the inner sleeve 150, the outer sleeve 155, and the opening device 135 lie close to the linear unit 165.

The first motion that is implemented according to this exemplary embodiment by rotating the rotary knob 125, is an abrupt, axial forward motion of the punching tool by 5 mm to 15 mm. The punching tool is simultaneously a punch and the implant device 105. It is a wire mesh that punches a hole into the blood vessel and is subsequently directly implanted. The compressed state of the wire mesh is more clearly apparent in FIG. 2. The outer sleeve 155 is positioned around the wire mesh during the punching process so that the wire mesh is provided with the stiffness required for punching. The outer sleeve 155 also prevents an unwanted, premature expansion of the wire mesh. Punching is carried out during the forward motion. An opening unit 192 comprising a barb, which is located within the punching wire mesh, move along with the implant device 105 into the blood vessel. After the punching process, the opening unit 192, including the barb and the punched-out tissue, is withdrawn and the wire mesh expands. The expansion of the wire mesh takes place by means of the retraction, i.e., the return motion, of the outer sleeve 155. With the aid of the acting radial force, the mesh is affixed on the blood vessel and simultaneously seals toward the outside. The abrupt opening motion of the linear unit 165 is implemented by the spring 170 which can be a compression spring and is located on the linear unit 165. The spring 170 was preloaded during installation by means of the plug-and-socket connection, i.e., the bayonet lock in this case. The bayonet lock is opened during the rotation of the rotary element 160 and the spring 170 is relaxed. The entire linear unit 165 moves axially along with the different tools in the form of the opening device 135, the inner sleeve 150 comprising the implant device 105, and the outer sleeve 150 by 5 mm to 12 mm. A hole has now been punched into the blood vessel and the wire mesh has been simultaneously implanted. The linear unit 165 is now rotated further. As a result, the two sleeves 150, 155, which are necessary for the expansion of the wire mesh, are retracted and the punching device 100 can be removed from the blood vessel. The two sleeves 150, 155 can be moved relative to each other. The outer sleeve 155 is retracted first, and so the wire mesh expands. Next, the inner sleeve 150, on which the wire mesh was located before the expansion, is retracted. A wire mesh which seals toward the outside is now located in the punched hole of the blood vessel, through which a supply cable can be routed. The mesh seals toward the inside only once the intended cable has been routed through. The aforementioned seal is not part of this approach, however. According to one alternative exemplary embodiment, the implant device 105 is tightly sealed without the cable passage. According to one alternative exemplary embodiment, the implant device 105 comprises a sealing unit which seals the hole during the implantation. Given that the implant device 105 is designed for deforming itself, the implant device 105 advantageously does not need to be deformed, for example, bent, by an external application of force during implantation.

The housing 130 of the punching device 100 consists of two housing halves which are connected to each other. Only one housing half is represented here, for the sake of clarity. Apart from the connection mechanism, the two housing halves are designed to be axially symmetrical with respect to each other.

The rotary knob can be replaced by the push-button when a preloaded torsion spring is relaxed by way of the actuation of the push-button.

This torsion spring then rotates the linear unit 165 at a previously calculated speed. Alternatively to the manual operation, the push-button can also be operated using a cordless screwdriver, which was designed especially for surgery, or using a screwdriver without a rechargeable battery.

Merely by way of example, the securing button has a length of 25 mm and a width of 10 mm, a securing-pin diameter is 3 mm, all other pins/cams 180, 190, 194 have a diameter of 3 mm, and the punching implant device 105 has an outer diameter of 3 mm to 7 mm and a length of 20 mm. Possible dimensions of the housing 130 of the punching device 100 are 212 mm×40 mm×28 mm (L×H×W). The rotary knob has a diameter of 40 mm to 50 mm, the linear unit 165 has a maximum diameter of 20 mm and a length (without the rotary knob) of 190 mm. The spring 170 has a length of 20 mm in the tensioned state 145 and a length of 40 mm in the relaxed state.

By way of example, the spring 170 is made of spring steel, the pins/cams 180, 190, 194 and the opening unit 192 comprising the barb are made of stainless steel, the implant device 105 is made of a wire mesh made of Nitinol, and a seal that is used is made of silicone. The further elements can be made of a biocompatible plastic, such as ABS M30i or the like.

Possible methods for producing the plastic parts include, in this case, by way of example, an injection molding process or 3D printing, for example, an FDM process.

Figure 2:
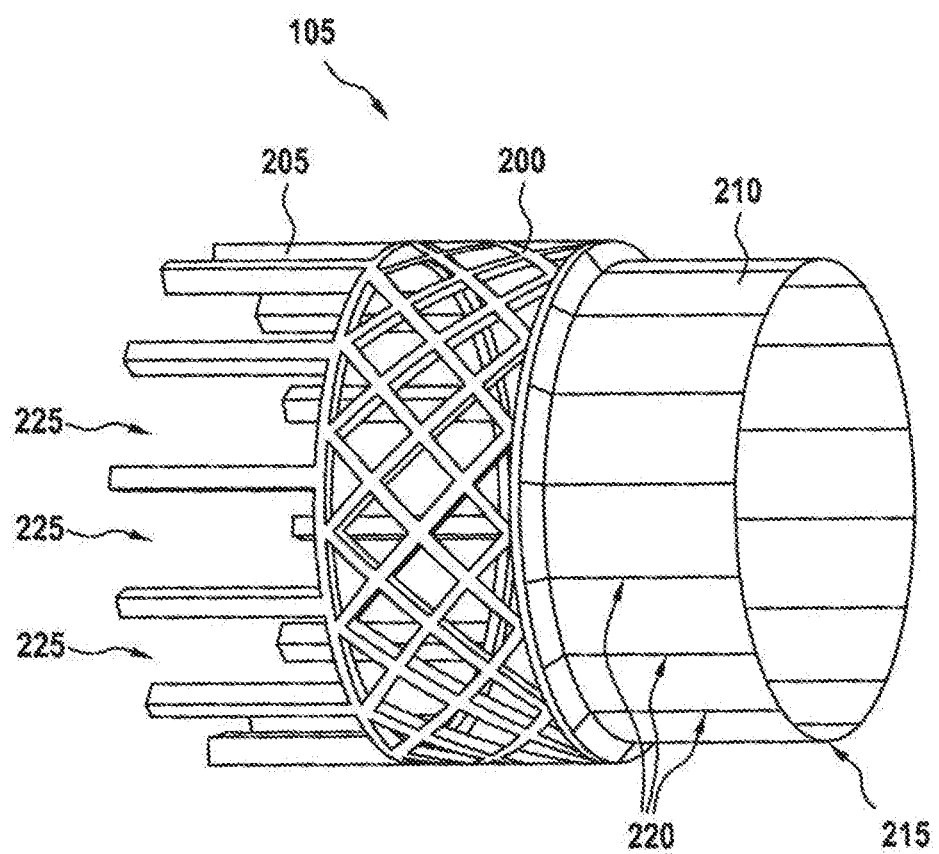
FIG. 2 shows a perspective side view of an implant device in an implantation device according to one exemplary embodiment.

FIG. 2 shows a perspective side view of an implant device 105 in an implantation device according to one exemplary embodiment.

The implant device 105 is disposed in the implantation device in the compressed state in which the implant device 105, according to this exemplary embodiment, is tubular overall. According to this exemplary embodiment, the implant device 105 comprises, in a central region, a wire mesh ring 200 from which a clamping section 205 extends in one direction and a punching section 210 extends in an opposite direction.

The punching section 210, in a state disposed in the punching device 100, faces the outlet opening and comprises a cutting edge 215 on a free end. The cutting edge 215 can also be referred to as a blade and is designed for punching the blood vessel by means of the forward motion. According to this exemplary embodiment, the punching section 210 comprises a plurality of longitudinal slots 220 and the clamping section 205 comprises a plurality of recesses 225. The longitudinal slots 220 and the recesses 225 allow for a deformation of the clamping section 205 and the punching section 210 during implantation of the implant device 105. The implant device 105 is represented in a deformed, implanted state in FIG. 4.

Figure 3:
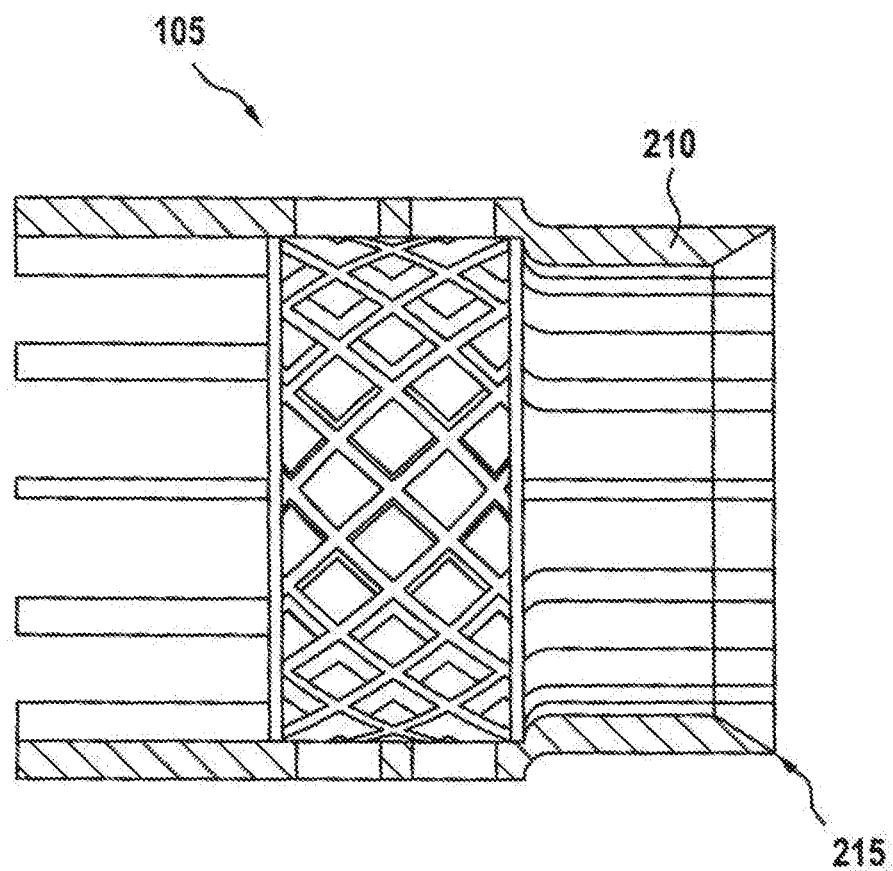
FIG. 3 shows a cross-section of a side view of an implant device in an implantation device according to one exemplary embodiment.

FIG. 3 shows a cross-section of a side view of an implant device 105 in an implantation device according to one exemplary embodiment. This can be the implant device 105 described with reference to FIG. 2.

The wire mesh is designed to be slanted and to have a sharp edge in the region of the cutting edge 215 so that punching is possible.

Figure 4:
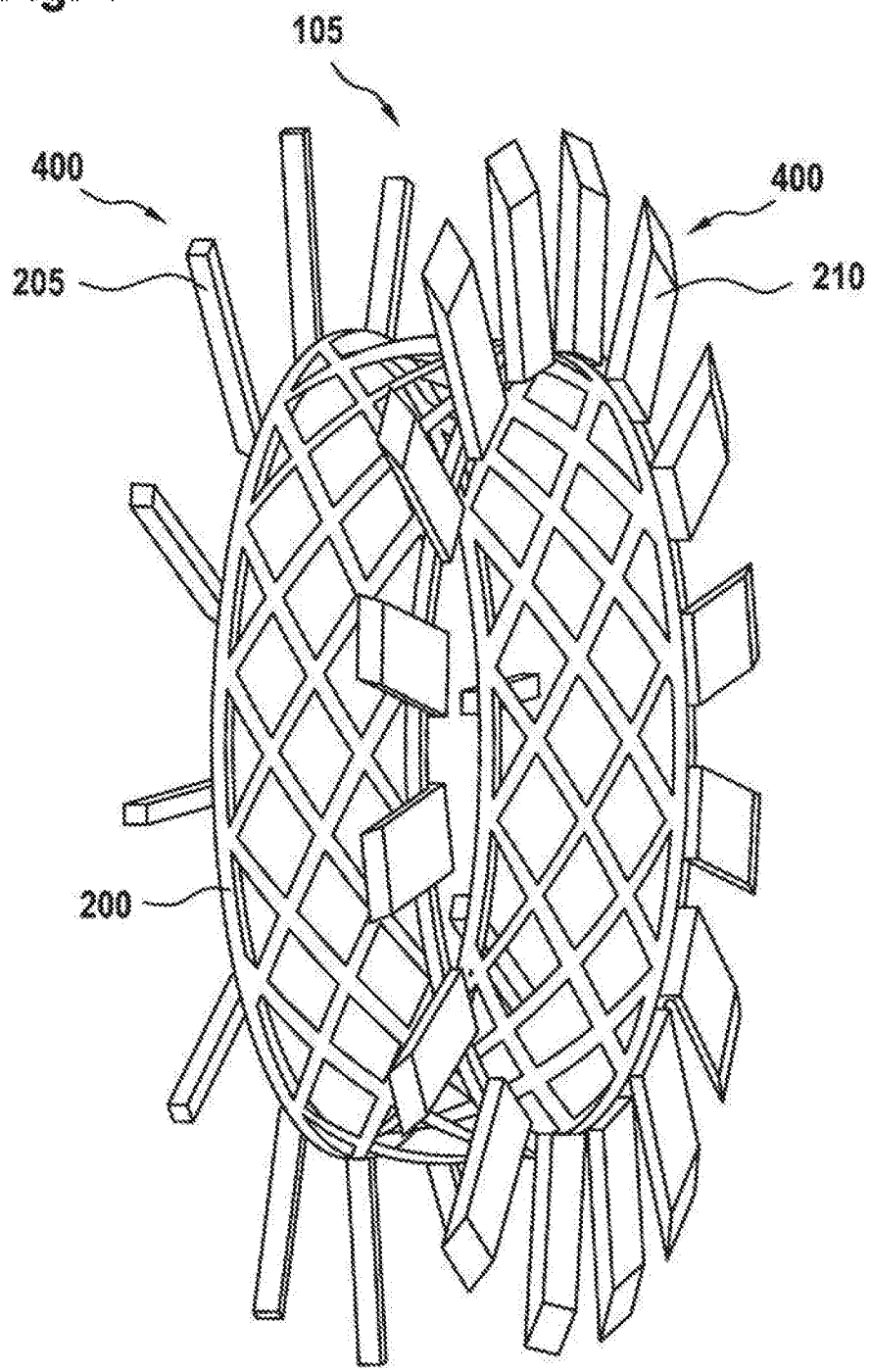
FIG. 4 shows a perspective side view of an implant device in an implanted state according to one exemplary embodiment.

FIG. 4 shows a perspective side view of an implant device 105 in an implanted state 400 according to one exemplary embodiment. This can be an implant device 105 described with reference to the preceding figures.

The clamping section 205 and the punching section 210 are shown deformed in the implanted state 400 after the return motion of at least the outer sleeve of the implantation device according to this exemplary embodiment. The clamping section 205 and the punching section 210 have deployed radially outwardly in this case by 90° around the wire mesh ring 200 according to this exemplary embodiment and are therefore each disposed perpendicular to the wire mesh ring 200. In the implanted state 400, the clamping section 205 and the punching section 210 are designed for fixedly clamping the implant device 105 in the blood vessel around the punched hole. The wire mesh ring 200 is deformed in an expanded state.

Figure 5:
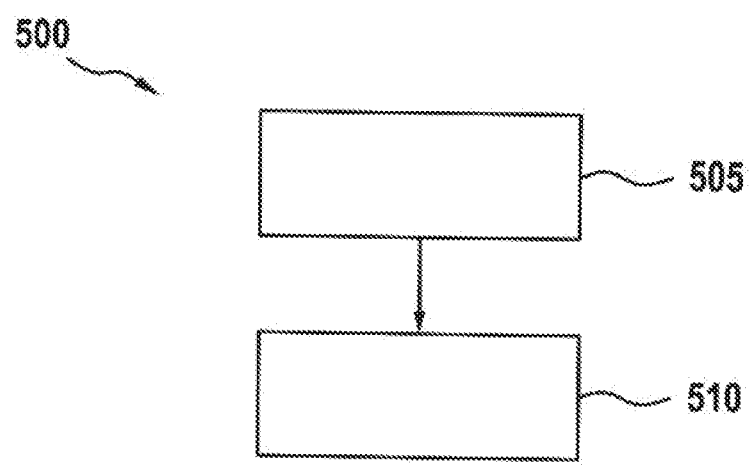
FIG. 5 shows a flow chart of a method for punching a lumen and implanting an implant device according to one exemplary embodiment.

FIG. 5 shows a flow chart of a method 500 for punching a lumen and implanting an implant device according to one exemplary embodiment. This can be a method 500 that can be implemented by the punching device described with reference to FIG. 1.

In a step 505 of bringing about, an opened state of a closure device is brought about for the purpose of releasing a restoring force for effectuating a forward motion of an implantation device coupled to the closure device, in order to punch the blood vessel by means of the the implant device coupled to the implantation device, wherein the opened state of the closure device is brought about by means of at least one actuation of an actuation device coupled to the closure device. In a step 510 of execution, a return motion of the implantation device is executed in order to effectuate an implantation of the implant device, which is coupled to the implantation device, into the punched blood vessel, wherein the return motion of the implantation device is executed by means of the at least one actuation of the actuation device.

If one exemplary embodiment has an "and/or" operation between a first feature and a second feature, this should be read to mean that the exemplary embodiment according to one exemplary embodiment comprises both the first feature and the second feature and, according to another exemplary embodiment, comprises either only the first feature or only the second feature.

The invention claimed is:

1. A method for implanting an implant device, comprising:
   bringing about an opened state of a closure device to release a restoring force by at least one actuation of an actuation device coupled to the closure device, the closure device being coupled to an implantation device;
   punching a lumen by the implant device coupled to the implantation device by effectuating a forward motion of the implantation device;
   executing a return motion of the implantation device by at least one actuation of the actuation device; and
   implanting the implant device into the lumen after punching the lumen;
   wherein punching the lumen comprises punching a hole in the lumen with a cutting edge of the implant device.

2. The method of claim 1, wherein implanting the implant device comprises implanting the implant device into the lumen through the hole.

3. The method of claim 2, wherein punching the hole comprises punching the implant device with the implantation device toward the lumen to cut the hole with the cutting edge and to position the implant device at least partially within the hole.

4. The method of claim 2, wherein the hole comprises a first hole, wherein the method further comprises opening a second hole in the lumen with at least one opening unit of an opening device before the cutting edge punches the hole in the lumen in response to the effectuating the forward motion of the implantation device, the opening device being coupled to the implantation device.

5. The method of claim 4, further comprising:
   captively fixing a lumen section of the lumen with a barb of the opening unit; and
   removing the lumen section from the lumen with barb while executing the return motion of the implantation device,
   wherein punching the first hole in the lumen with the cutting edge comprises punching the lumen section of the lumen with the cutting edge.

6. The method of claim 4, wherein the opening device is disposed at least partially in at least one of the implantation device or the implant device.

7. The method of claim 1, wherein bringing about the opened state of the closure device to release a restoring force comprises releasing a restoring force of a spring of the closure device, and wherein releasing the restoring force of the spring of the closure device is configured to effectuate the forward motion of the implantation device.

8. The method of claim 1, wherein the implantation device comprises:
   at least one inner sleeve being configured to guide the implant device; and
   an outer sleeve being configured to surround the implant device and to surround the inner sleeve in an at least partially linearly movable manner.

9. The method of claim 8, wherein executing the return motion comprises utilizing the outer sleeve to carry out the return motion.

10. The method of claim 1, wherein the implant device comprises a mesh having shape memory.

11. The method of claim 1, wherein:
    the closure device comprises a bayonet lock including a rotatable rotary element and a rotatable and linearly movable linear unit, and
    a spring is loaded in a closed state of the bayonet lock in order to generate the restoring force.

12. The method of claim 11, wherein bringing about the opened state of the closure device comprises transferring the bayonet lock from the closed state into the opened state by rotating the rotary element, and wherein effectuating the forward motion of the implantation device comprises executing a linear opening motion of the linear unit in a direction of an outlet opening of a punching device when the bayonet lock is transferred into the opened state.

13. The method of claim 11, wherein, in order to couple the closure device to the implantation device, at least one sleeve of the implantation device comprises at least one pin to be accommodated in at least one guide groove of the rotatable and linearly movable linear unit and/or the rotatable and linearly movable linear unit comprises at least the guide groove for accommodating the pin of the sleeve, and wherein the guide groove and the pin are configured such that, in the coupled state, the guide groove and the pin effectuate the return motion of the implantation device in response to the actuation of the actuation device after the lumen has been punched.

14. The method of claim 1, wherein the actuation device comprises at least one rotary knob configured to effectuate the at least one actuation of the actuation device in response to a rotary actuation.

15. The method of claim 1, wherein the actuation device comprises at least one push-button configured to effectuate the at least one actuation of the actuation device in response to a push actuation.

16. The method of claim 1, wherein at least the implant device and the implantation device are disposed on one axis.

17. The method of claim 1, wherein the lumen is one of a blood vessel, a stomach, an intestine, or a trachea.

18. The method of claim 17, wherein the lumen is a blood vessel.

* * * * *